(12) United States Patent
Dowling et al.

(10) Patent No.: US 8,664,199 B2
(45) Date of Patent: Mar. 4, 2014

(54) METHOD AND SYSTEM FOR REVERSAL OF INTERACTIONS BETWEEN HYDROPHOBICALLY MODIFIED BIOPOLYMERS AND VESICLES OR CELL MEMBRANES

(75) Inventors: Matthew Dowling, Washington, DC (US); Srinivasa R. Raghavan, Silver Spring, MD (US); Rakesh Kumar, Hillsboro, NC (US)

(73) Assignee: University of Maryland, College Park, College Park, MD (US)

( * ) Notice: Subject to any disclaimer, the term of this patent is extended or adjusted under 35 U.S.C. 154(b) by 113 days.

(21) Appl. No.: 13/209,399

(22) Filed: Aug. 13, 2011

(65) Prior Publication Data

US 2012/0058970 A1 Mar. 8, 2012

Related U.S. Application Data

(60) Provisional application No. 61/373,600, filed on Aug. 13, 2010.

(51) Int. Cl.
*A61K 31/722* (2006.01)

(52) U.S. Cl.
USPC ............................................................ 514/55

(58) Field of Classification Search
USPC ............................................................ 514/55
See application file for complete search history.

(56) References Cited

U.S. PATENT DOCUMENTS

| | | | |
|---|---|---|---|
| 4,532,134 A | 7/1985 | Malette et al. | |
| 4,572,906 A | 2/1986 | Sparkes et al. | |
| 4,752,466 A | 6/1988 | Saferstein et al. | |
| 4,895,724 A | 1/1990 | Cardinal et al. | |
| 5,243,094 A | 9/1993 | Borg | |
| 5,426,182 A | 6/1995 | Jenkins et al. | |
| 5,900,479 A | 5/1999 | Glasser et al. | |
| 5,919,574 A | 7/1999 | Hoagland | |
| 6,140,089 A | 10/2000 | Aebischer et al. | |
| 6,371,975 B2 | 4/2002 | Cruise et al. | |
| 6,458,147 B1 | 10/2002 | Cruise et al. | |
| 6,548,081 B2 | 4/2003 | Sadozai et al. | |
| 6,602,952 B1 | 8/2003 | Bentley et al. | |
| 6,663,653 B2 | 12/2003 | Akerfeldt | |
| 6,827,727 B2 | 12/2004 | Stalemark et al. | |
| 6,830,756 B2 | 12/2004 | Hnojewyj | |
| 6,864,245 B2 | 3/2005 | Vournakis et al. | |
| 6,890,344 B2 | 5/2005 | Levinson | |
| 6,899,889 B1 | 5/2005 | Hnojewyj et al. | |
| 6,949,114 B2 | 9/2005 | Milo et al. | |
| 6,958,325 B2 | 10/2005 | Domb | |
| 6,994,686 B2 | 2/2006 | Cruise et al. | |
| 6,995,137 B2 | 2/2006 | You et al. | |
| 7,247,314 B2 | 7/2007 | Hnojewyj et al. | |
| 7,279,001 B2 | 10/2007 | Addis et al. | |
| 7,288,532 B1 | 10/2007 | Payne et al. | |
| 7,318,933 B2 | 1/2008 | Hnojewyj | |
| 7,351,249 B2 | 4/2008 | Hnojewyj et al. | |
| 7,482,503 B2 | 1/2009 | Gregory et al. | |
| 7,820,872 B2 | 10/2010 | Gregory et al. | |
| 2002/0028181 A1 | 3/2002 | Miller et al. | |
| 2002/0068151 A1 | 6/2002 | Kim et al. | |
| 2004/0001893 A1 | 1/2004 | Stupp | |
| 2005/0038369 A1 | 2/2005 | Gregory et al. | |
| 2005/0147656 A1 | 7/2005 | McCarthy et al. | |
| 2005/0181027 A1 | 8/2005 | Messinger | |
| 2006/0094060 A1 | 5/2006 | Jarhede et al. | |
| 2006/0167116 A1 | 7/2006 | Uchegbu et al. | |
| 2006/0269485 A1 | 11/2006 | Friedman et al. | |
| 2007/0055364 A1 | 3/2007 | Hossainy | |
| 2007/0148215 A1 | 6/2007 | Teslenko et al. | |
| 2008/0103228 A1 | 5/2008 | Falcone et al. | |
| 2008/0254104 A1* | 10/2008 | Raghavan et al. | 424/445 |
| 2009/0062849 A1* | 3/2009 | Dowling et al. | 606/214 |
| 2009/0192429 A1 | 7/2009 | Daniels et al. | |
| 2009/0226391 A1 | 9/2009 | Roberts et al. | |
| 2011/0052665 A1 | 3/2011 | Hardy et al. | |
| 2011/0217785 A1 | 9/2011 | Liu et al. | |
| 2012/0058970 A1 | 3/2012 | Dowling | |
| 2012/0252703 A1 | 10/2012 | Dowling | |

OTHER PUBLICATIONS

Kubota et al. Gelation dynamics and gel structure of fibrinogen. Colloids Surf B Biointerfaces 38:103-109, 2004.*
Chiaki Yoshina-Ishii and Steven G. Boxer, Arrays of Mobile Tethered Vesicles on Supported Lipid Bilayers, J. Am. Chem. Soc. 125(13):3696-3697 (2003).
Yoshina-Ishii et al.,General Method for Modification of Liposomes for Encoded Assembly on Supported Bilayers, J. Am. Chem. Soc. 127(5):1356-1357 (2005).

(Continued)

*Primary Examiner* — Wu-Cheng Winston Shen
*Assistant Examiner* — Yih-Horng Shiao
(74) *Attorney, Agent, or Firm* — Whiteford, Taylor & Preston, LLP; Joseph L. Morales

(57) ABSTRACT

A method for reversing gelation of hydrophobically modified biopolymer attached to vesicle or cell membranes. The gelation of hydrophobically modified biopolymer attached to vesicles or cell membranes is reversed by application of a supramolecule, such as cyclodextrin, to the gelled composition. The supramolecule disrupts the interactions between the hydrophobically modified biopolymer and the vesicle or cell membrane, without affecting the structure of the membrane or the hydrophobically modified polymer to which the hydrophobic substituents are attached. A kit for treating wounds that includes a hydrophobically modified biopolymer and a supramolecule. The hydrophobically modified biopolymer is used to stop bleeding and the supramolecule is used to remove the hydrophobically modified biopolymer.

17 Claims, 7 Drawing Sheets

(56) References Cited

OTHER PUBLICATIONS

Yoshina-Ishii et al.,Diffusiye Dynamics of Vesicles Tethered to a Fluid Supported Bilayer by Single-Particle Tracking, Langmuir 22(13):5682-5689 (2006).

Esquenet et al.,Structural and Rheological Properties of Hydrophobically Modified Polysaccharide Associative Networks, Langmuir 20(9):3583-3592 (2004).

Ankit R. Patel and Curtis W. Frank, Quantitative Analysis of Tethered Vesicle Assemblies by Quartz Crystal Microbalance with Dissipation Monitoring: Binding Dynamics and Bound Water Content, Langmuir 22(18):7587-7599 (2006).

Jung et al., Quantification of Tight Binding to Surface-Immobilized Phospholipid Vesicles Using Surface Plasmon Resonance: Binding Constant of Phospholipase A2, J. Am. Chem. Soc. 122(17):4177-4184 (2000).

Boukobza et al., Immobilization in Surface-Tethered Lipid Vesicles as a New Tool for Single Biomolecule Spectroscopy, J. Phys. Chem. B 105(48):12165-12170 (2001).

Hook et al., Supported Lipid Bilayers, Tethered Lipid Vesicles, and Vesicle Fusion Investigated Using Gravimetric, Plasmonic, and Microscopy Techniques, Biointerphases 3(2) (Jun. 2008).

Khan et al., Mechanical, Bioadhesive Strength and Biological Evaluations of Chitosan Films for Wound Dressing, J. Pharm. Pharmaceut. Sci. 3(3):303-311 (2000).

Tanweer A. Khan and Kok Khiang Peh, A Preliminary Investigation of Chitosan Film as Dressing for Punch Biopsy Wound in Rats, J. Pharm. Pharmaceut. Sci. 6(1):20-26 (2003).

Anderluh et al., Properties of Nonfused Liposomes Immobilized on an L1 Biacore Chip and Their Permeabilization by a Eukaryotic Pore-forming Toxin, Anal. Biochem. 344:43-52 (2005).

New! Pioneer Chip L1 Improved binding studies in model membrane systems, BIA Journal No. 2 1998.

Lunelli et al., Covalently Anchored Lipid Structures on Amine-Enriched Polystyrene, Langmuir 21(18):8338-8343 (2005).

Kjoniksen et al., Light Scattering Study of Semidilute Aqueous Systems of Chitosan and Hydrophobically Modified Chitosans, Macromolecules 31(23):8142-8148 (1998).

Wu et al., Voltage-Dependent Assembly of the Polysaccharide Chitosan onto an Electrode Surface, Langmuir 18 (22):8620-8625 (2002).

Fernandes et al., Electrochemically Induced Deposition of a Polysaccharide Hydrogel onto a Patterned Surface, Langmuir 19(10):4058-4062 (2003).

Wu et al., Spatially Selective Deposition of a Reactive Polysaccharide Layer onto a Patterned Template, Langmuir 19 (3):519-524 (2003).

Zhu et al., Reversible Vesicle Restraint in Response to Spatiotemporally Controlled Electrical Signals: A Bridge between Electrical and Chemical Signaling Modes, Langmuir 23(1) 286-291 (2007).

Gregory F. Payne and Srinivasa R. Raghavan, Chitosan: a Soft Interconnect for Hierarchical Assembly of Nano-scale Components, Soft Matter 3:521-527 (2007).

Lee et al., Vesicle-Biopolymer Gels: Networks of Surfactant Vesicles Connected by Associating Biopolymers, Langmuir 21(1):26-33 (2005).

Zhu et al., Bioinspired Vesicle Restraint and Mobilization Using a Biopolymer Scaffold, Langmuir 22(7):2951-2955 (2006).

Lee et al., Transition from Unilamellar to Bilamellar Vesicles Induced by an Amphiphilic Biopolymer, Phys. Review Letters, 96:048102-1-048102-4 (2006).

Desbrieres et al., Hydrophobic Derivatives of Chitosan: Characterization and Rheological Behaviour, Biological Macromolecules, 19:21-28 (1996).

Cooper et al., A Vesicle Capture Sensor Chip for Kinetic Analysis of Interactions with Membrane-Bound Receptors, Anal. Biochem. 277:196-205 (2000).

Tangpasuthadol, Surface Modification of Chitosan Films. Effects of Hydrophobicity on Protein Adsorption, Carbohydrate Res. 338:937-942 (2003).

Stavroula Sofou and James L. Thomas, Stable Adhesion of Phospholipid Vesicles to Modified Gold Surfaces, Biosensors and Bioelectronics 18:445-455 (2003).

Mansur Yalpani and Laurence D. Hall, Some Chemical and Analytical Aspects of Polysaccharide Modifications. Formation of Branched-Chain, Soluble Chitosan Derivatives, Macromolecules 17(3):272-281 (1984).

Paul S. Cremer and Steven G. Boxer, Formation and Spreading of Lipid Bilayers on Planar Glass Supports, J. Phys. Chem. B 103(13):2554-2559 (1999).

Li et al., Multivesicular Liposomes for Oral Delivery of Recombinant Human Epidermal Growth Factor, Arch Pharm Res 28(8):988-994 (2005).

Koehler et al., Microstructure and Dynamics of Wormlike Micellar Solutions Formed by Mixing Cationic and Anionic Surfactants, J. Phys. Chem. B 104(47):11035-11044 (2000).

Kaler et al., Spontaneous Vesicle Formation in Aqueous Mixtures of Single-Tailed Surfactants, Science 245(4924): 1371-1374 (1989).

Kaler et al., Phase Behavior and Structures of Mixtures of Anionic and Cationic Surfactants, J. Phys. Chem. 96(16): 6698-6707 (1992).

Fu et al., Protein stability in controlled-release systems, Nature Biotechnology 18:24-25 (2000).

D. D. Lasic and D. Papahadjopoulos, Liposomes Revisited, Science 267(5202):1275-1276 (1995).

Dan D. Lasic, Novel Applications of Liposomes, Trens in Biotechnology (TIBTECH) 16:307-321 (1998).

Hong et al., Two-step Membrane Binding by Equinatoxin II, a Pore-forming Toxin from the Sea Anemone, Involves an Exposed Aromatic Cluster and a Flexible Helix, J. Biol. Chem. 277(44):41916-41924 (2002).

Naumann et al., Proton Transport Through a Peptide-tethered Pilayer Lipid Membrane by the H±ATP Synthase from Chloroplasts Measured by Impedance Spectroscopy, Biosensors and Bioelectronics 17:25-34 (2002).

Nikolelis et al., A Minisensor for the Rapid Screening of Sucralose Based on Surface-stabilized Bilayer Lipid Membranes, Biosensors & Bioelectronics 15:439-444 (2000).

Mathivet et al., Shape Change and Physical Properties of Giant Phospholipid Vesicles Prepared in the Presence of an AC Electric Field, Biophysical Journal 70:1112-1121 (1996).

Puu et al., Retained Activities of Some Membrane Proteins in Stable Lipid Bilayers on a Solid Support, Biosensors and Bioelectronics 10:463-476 (1995).

Szymanska et al., Fullerene Modified Supported Lipid Membrane as Sensitive Element of Sensor for Odorants, Biosensors & Bioelectronics 16:911-915 (2001).

Rongen et al., Liposomes and Immunoassays, J. Immunol. Methods 204:105-133 (1997).

Michael I. Fisher and Torbjorn Tjarnhage, Structure and Activity of Lipid Membrane Biosensor Surfaces Studied with Atomic Force Microscopy and a Resonant Mirror, Biosensors & Bioelectronics 15:463-471 (2000).

Zhdanov et al., Comments on Rupture of Adsorbed Vesicles (Langmuir 2001, 17, 3518-3521).

Zhdanov et al. Adsorption and Spontaneous Rupture of Vesicles Composed of Two Types of Lipids (Langmuir 2006, 22, 3477-3480).

Dimitrievski et al., Influence of Lipid-Bilayer-Associated Molecules on Lipid-Vesicle Adsorption (Langmuir 2010, 26 (8), 5706-5714).

Allerbo et al., Simulation of lipid vesicle rupture induced by an adjacent supported lipid bilayer patch (Colloids and Surfaces B: Biointerfaces 2011, 82, 632-636).

Dimitrievski et al., Simujlations of Lipid Vesicle Adsorption for Different Lipid mixtures (Langmuir 2008, 24, 4077-4091).

Alam, Hasan B., et al. Comparative Analysis of Hemostatic Agents in a Swine Model of Lethal Groin Injury, J. Trauma 54:1077-1082 (2003).

Brandenberg, Greg et al. Chitosan: A New Tropical Hemostatic Agent for Diffuse Capillary Bleeding in Brain Tissue, Neurosurgery 15(1): 9-13 (1984).

(56) References Cited

OTHER PUBLICATIONS

Burkatovskaya, Marina et al., Use of Chitosan Bandage to Prevent Fatal Infections Developing From Highly Contaminated Wounds in Mice, Biomaterials 27:4157-4164 (2006).

Chenite, A. et al "Rheological characterization of thermogelling chitosan/glycerol-phosphate solutions" Carbohydrate Polymers 46, 39-47 (2001).

Coster, Bag-On-Valve Series Offers Faster Filling and Better Drop Resistance. 2007. Downloaded from the world wide web on Jan. 18, 2012 <http://www.coster.com/news/eng/2007-10-18_AE_bov/AE_Manchester_BOV_eng.pdf.>.

Eldin, Mohy et al. Chitosan Modified Membranes for Wound Dressing Applications: Preparations, Characterization and Bio-Evaluation. Trend Biomater. Atif.Organs. vol. 22 (3). pp. 158-168, 2008.

GlaxoSmithKline. Bactroban Ointment: Prescribing Information. Research Triangle Park, NC, May 2005. Downloaded from the world wide web on Jan. 17, 2013 <https://www.gsksource.com/gskprm/htdocs/documents/BACTROAN-OINTMENTS.PDF>.

Hirano and Noishiki, The Blood Compatibility of Chitosan and N-Acylchitosans, J. Biochem. Materials Res. 413-417 (1985).

Hou, et al. "Preparation and characterization of RGD-immobilized chitosan scaffolds," Biomaterials 26 (2005) 3197-3206, published Oct. 14, 2004.

Kheirabadi, Bijan S. et al., Hemostatic Efficacy of Two Advanced Dressings in an Aortic Hemorrhage Model in Swine, J. Trauma Injury, Infection, and Critical Care, 59:25-35 (2005).

Kozen, Buddy G. et al., An Alternative Hemostatic Dressing: Comparison of CELOX, HemCon, and QuikClot, Acad. Emerg. Med. 15:74-81(2008).

Lu, S. et al. "Preparation of Water-Soluble Chitosan" Journal of Applied Polymer Science 91, 3497-2503 (2004).

Li, et al. "Multivesicular Liposomes for Oral Delivery of Recombinant Human Epidermal Growth Factor." Archives of Pharmacal Research, 2005, 28, 8, 988-994.

Malette, William G. et al. Chitosan: A New Hemostatic, The Annals of Thoracic Surgery 36(1):55-58 (1983).

Meier, Wolfgang et al., Vesicle and Cell Networks: Interconnecting Cells by Synthetic Polymers, Langmuir 12:5028-5032 (1996).

Rodriguez, M.S., et al "Interaction between chitosan and oil under stomach and duodenal digestive chemical conditions" Biosci. Biotechnol. Biochem. 69 (11), 2057-2062 (2005).

Whang, Hyun Suk et al., Hemostatic Agents Derived from Chitin and Chitosan, J. Macromolecular Science 45:309-323 (2005).

Zhang, Jing. Drug Delivery: Self-Assembled Nanoparticles based on Hydrophobically Modified chitosan as Carriers for Doxorubicin, Nanomedicine, Elsevier. Aug. 2007. pp. 258-265.

Office Action issued in related U.S. Appl. No. 12/946,818 on May 14, 2012.

Office Action issued in related U.S. Appl. No. 12/946,818 on Jan. 28, 2013.

Office Action issued in related U.S. Appl. No. 12/231,571 on Mar. 5, 2012.

Office Action issued in related U.S. Appl. No. 12/231,571 on Sep. 21, 2012.

Office Action issued in related U.S. Appl. No. 12/077,173 on Nov. 8, 2010.

Office Action issued in related U.S. Appl. No. 12/077,173 on Apr. 14, 2011.

Office Action issued in related U.S. Appl. No. 13/310,579 on Apr. 11, 2013.

\* cited by examiner

METHOD AND SYSTEM FOR REVERSAL OF INTERACTIONS BETWEEN HYDROPHOBICALLY MODIFIED BIOPOLYMERS AND VESICLES OR CELL MEMBRANES

CROSS REFERENCE TO RELATED APPLICATION

The present application claims priority under 35 U.S.C. §119 to the U.S. Provisional Application Ser. No. 61/373,600 filed on Aug. 13, 2010, which is incorporated herein by reference in its entirety.

FIELD OF THE INVENTION

The present invention generally relates to the field of hydrophobically modified polymers and their interactions with cells and vesicle membranes. In particular, this invention relates to a method and system that specifically reverses the interaction between hydrophobically modified biopolymers and cell or vesicle membranes.

BACKGROUND OF THE INVENTION

The blood coagulation cascade is an exquisite example of a responsive self-assembly process in biology.[1,2] When a wound is formed, a cascade of self-assembly events occur in blood at the site of the wound. The net outcome is the assembly of the globular protein, fibrinogen, catalyzed by a second protein, thrombin to yield chains of fibrin.[3,4] A network of insoluble fibrin chains forms a hemostatic "plug" or clot, which presents a physical barrier to the loss of blood from the wound.[1,2] The coagulation cascade is a delicately balanced series of events—if it was to occur too easily, blood clots may form in unwanted areas leading to strokes or other complications.

Scientists have long sought to harness the clotting power of fibrin to create hemostatic dressings or bandages.[5-7] Hemostatic dressings that can staunch the bleeding from serious wounds are a pressing need both in civilian trauma centers as well as for military personnel. Indeed, uncontrolled hemorrhage from severe injuries is a leading cause of death among young adults (e.g., accident victims) and it is also responsible for the majority of deaths on the battlefield.[8-10] Fibrin-based hemostatic sealants were first-developed in the 1940s and have proven to be quite effective.[6,7] For example, one form involves a dry powdered mixture of human fibrinogen and thrombin packed onto a solid bandage backing. When such a bandage is firmly pressed onto a bleeding injury, a strong fibrin seal quickly forms and bleeding is stopped.[6] However, fibrin bandages have limited practical applicability in trauma medicine because human fibrinogen and thrombin are highly expensive molecules that are scarce in supply.[7]

A need thus exists for an inexpensive hemostatic agent based on widely-available materials that could match the blood-clotting ability of fibrin. Although a variety of hemostats have been brought to market,[5,11-15] none have shown the efficacy of fibrin sealants.[11,12] Several products work simply by absorbing the blood at the site of the wound rather than by coagulating the blood.[12,14] Recently, a new approach has been put forward by Ellis-Behnke et al.,[16] wherein the self-assembly of a synthetic peptide into a nano-fibrous network[17] is used to achieve hemostasis independent of the natural coagulation cascade. While this method is promising, the synthetic peptides employed are expensive and difficult to synthesize—therefore their practical viability is unclear. An additional factor to consider with hemostats such as the above is the risk of undesired gelation or clotting, i.e., embolization, in parts of the body that are peripheral to the site of injury.[14,18] To mitigate against such risks, it would be desirable to have the hemostat disassemble or "unclot" if and when desired; however, none of the hemostats described in the literature have been shown to have this ability.

SUMMARY OF THE INVENTION

One embodiment of the present invention provides a method for reversing the interaction between a hydrophobically modified polymeric matrix (e.g., hm-chitosan) and membranes (cell membranes or vesicle membranes), which form a gelled matrix. In accordance with the method a supramolecule capable of disrupting interactions between hydrophobic substituents on the hydrophobically modified polymeric matrix, without affecting the structure of the membrane or the hydrophobically modified polymer to which the hydrophobic substituents are attached, is applied to the gelled matrix and cell or vesicle membranes. In one such embodiment, the supramolecule is a cyclodextrin, which may be selected from the group consisting of α-CD, β-CD, γ-CD, methyl-β-CD, 2-hydroxypropyl-β-CD, 2-hydroxypropyl-γ-CD, sulfobutylether-β-CD and other cyclodextrin derivatives.

A further embodiment of the present invention provides a kit for treating wounds. The kit has several components, including a hydrophobically modified polymeric matrix for application to a wound and a supramolecule to reverse the interactions between the cells at the wound site and the hydrophobically modified polymeric matrix.

In yet a further embodiment, a method for treating wounds is presented in which the first step is to apply a hydrophobically modified matrix, e.g., hm-chitosan, to a wound. The hydrophobically modified matrix is applied in the form of a bandage, a gel, a liquid in spray or through a syringe, or in liquid form directly on the wound. Once the wound has healed or when the treatment is to be removed, in a second step, a supramolecule, e.g., cyclodextrin, is applied to the wound, releasing the hydrophobically modified matrix. The supramolecule is applied in the form of a liquid solution through a syringe, spray, or directly on the wound.

BRIEF DESCRIPTION OF THE DRAWINGS

The numerous advantages of the present invention may be better understood by those skilled in the art by reference to the accompanying figures in which.

DETAILED DESCRIPTION OF THE INVENTION

Figure 1:
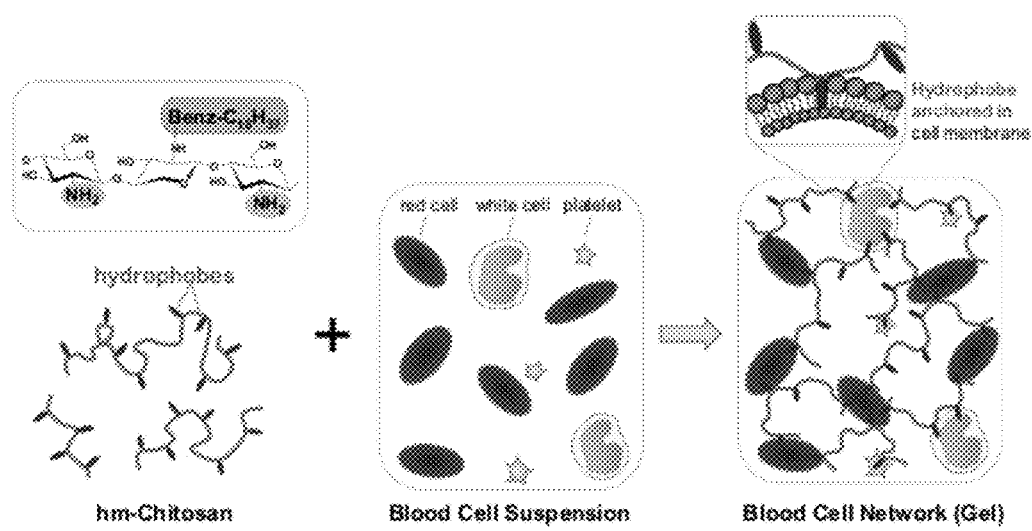
FIG. 1 is a graphical representation of gelling by interactions between hm-chitosan and cell membranes.

The following description is of a particular embodiment of the invention, set out to enable one to practice an implementation of the invention, and is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

The Applicants describe a type of self-assembling molecule which is able to halt blood flow via barrier formation, but yet retains the versatility to disassemble these barriers on demand. These molecules are hydrophobically-modified biopolymers, as described below, and they are able to form gel barriers by crosslinking of blood cells and other vesicles into 3-dimensional matrices via hydrophobic interactions with cell membranes. The applicants show that such gels are reverted into a flowing state upon introduction of supramolecules such as cyclodextrins into the gelled system. These supramolecules contain accessible hydrophobic "pockets" that specifically sequester the hydrophobic substituents on the biopolymer backbone, thus eliminating the gel-forming interactions between hydrophobic substituents and cellular or vesicular membranes.

The applicants further describe a method for reversing the formation of a gel between a biopolymeric matrix and cells or vesicles. The biopolymeric matrix or hemostatic material consists of at least one polymer and plurality of short hydrophobic substituents attached along the polymer backbone as described in United States Patent Application Publication Numbers US2008/0254104A1 and US2009/0062849A1, both of which are incorporated herein by reference in their entirety. The polymer is either synthetic or naturally occurring, including, for example, water-soluble polysaccharides and polypeptides. In exemplary embodiments, the polymer is one or more hydrophobically-modified polysaccharides selected from the group consisting of cellulosics, chitosans and alginates. Cellulosics, chitosans and alginates are all abundant, natural polymers. Cellulosics are found in plants, whereas chitosans and alginates are found in the exoskeleton or outer membrane of a variety of living organism. All three types of materials allow for the transfer of oxygen and moisture required for wound healing metabolism. Chitosan also has inherent anti-microbial properties, [19,22-24] which is an important asset for materials covering open wounds because it eliminates the need to constantly change wound dressings in order to disinfect the wound manually between changes. Positive charges along the backbone of chitosan cause it to interact electrostatically with negatively charge blood cells, thus creating a sticky interface between a chitosan dressing and the wound. Chitosan provides hemostasis to severe hemorrhage injuries for a period of 30-45 min before becoming saturated with blood and losing adhesion to the injury site. Native chitosan, however, does not form gels when combined with blood.

Cellulosics include, for example, hydroethyl cellulose, hydroxypropyl cellulose, methyl cellulose, hydroxypropyl methyl cellulose, hydroxyethly methyl cellulose, etc. Chitosans include, for example, the following chitosan salts: chitosan lactate, chitosan salicylate, chitosan pyrrolidone carboxylate, chitosan itaconate, chitosan niacinate, chitosan formate, chitosan acetate, chitosan gallate, chitosan glutamate, chitosan maleate, chitosan aspirate, chitosan glycolate and quaternary amine substituted chitosan and salts thereof, etc. Alginates include, for example, sodium alginate, potassium alginate, magnesium alginate, calcium alginate and aluminum alginate, etc. In an example, the polymeric component of the dressing comprises mixtures of polysaccharides between classes, e.g. cellulosics and chitosan, or within the same class, e.g. two alginates.

A hydrophobic substituent (also referred to as a hydrophobic tail) comprising a hydrocarbon group having from about 2 to about 50 carbon atoms, more preferably 6 to 36 carbon atoms is attached to the backbone of at least one polymer. In a further embodiment, the hydrophobic substituents are hydrocarbon groups having 8 to 24 carbon atoms. In an exemplary embodiment, the hydrocarbon group comprises an alkyl or aryl group. As used herein, the term "arylalkyl group" means a group containing both aromatic and aliphatic structures. Examples of procedures for modifying polymers are as follows:

1) Alginates are hydrophobically modified by exchanging their positively charged counterions (e.g. $Na^+$) with tertiary-butyl ammonium ($TBA^+$) ions using a sulfonated ion exchange resin. The resulting TBA-alginate is dissolved in dimethylsulfoxide (DMSO) where reaction occurs between alkyl (or aryl) bromides and the carboxylate groups along the alginate backbone.
2) Cellulosics are hydrophobically-modified by first treating the cellulosic material with a large excess of highly basic aqueous solution (e.g. 20 wt % sodium hydroxide in water). The alkali cellulose is then removed from solution and vigorously mixed with an emulsifying solution (for example, oleic acid) containing the reactant, which is an alkyl (or aryl) halide (e.g. dodecyl bromide).
3) Chitosans are hydrophobically-modified by reaction of alkyl (or aryl) aldehydes with primary amine groups along the chitosan backbone in a 50/50 (v/v) % of aqueous 0.2 M acetic acid and ethanol. After reaction, the resulting Schiff bases, or imine groups, are reduced to stable secondary amines by drop wise addition of the reducing agent sodium cyanoborohydride or sodium triacetoxyborohydride. When the biopolymer used is chitosan, the hydrophobically-modified biopolymer is referred to as hm-chitosan.[20,21]

These hydrophobically modified polymers cause the gelation of bilayer enclosed structures such as vesicles and cells by means of an energetically driven self-assembly process. As utilized in this application, the term "vesicle" refers to any hollow spherical structures formed by the self-assembly of surfactants, lipids, or block copolymers in aqueous solution. Vesicles are of technological interest for applications ranging from drug delivery and controlled release to bioseparations and sensing. Many of these applications rely upon the ability of vesicles to entrap desired chemicals (i.e., functionalization) in their interior and thereafter release these chemicals to the external medium in a controlled manner. The biological cell, which is the building block of any living organism, is also a bilayer enclosed structure, much like a vesicle. The term "cell", as used in this application, refers to any biological cell, e.g. fibroblasts, HeLa cells, endothelial cells, red blood cells, white blood cells, platelets, cancer cells, osteoblasts, epithelial cells, of any living species.

Gels form by the physical bridging of cells and/or vesicles into a 3-dimensional network via insertion of hydrophobic substituents/tails grafted onto hydrophilic polymer backbones into the cell and/or vesicle bilayers. The cells and/or vesicles act as physical crosslinks in the network and the polymers act as bridges between the crosslinks as shown on FIG. 1. As referred to in this application, "membranes" are the bilayers that form the outer surface of cells and vesicles. Membranes in the exterior of cells are referred to as "cellular membranes" and the membranes that form the exterior of vesicles are referred to as "vesicle membranes." The hm-chitosan is combined with a blood cell suspension that contains red blood cells, white blood cells, and platelets. The hydrophobic tails or substituents are integrated within the interior of the cell membrane, creating a blood cell network in the form of a gel or clot. Applicants have previously described a blood clotting and tissue adhesion mechanism orchestrated by the self-assembly of amphiphilic polymers, e.g. hydrophobically modified chitosan, into a 3-dimensional matrix. US2008/0254104A1 and US2009/0062849A1. Hemostasis, or stoppage of blood flow, provided by amphiphilic polymers is driven by the gelation of blood resulting from the hydrophobic affinity between grafted alkyl tails on the polymer backbone and the acyl tails of lipids in cell bilayers.

The Applicants have discovered that this gelation is readily reversed by introduction of an amphiphilic supramolecule. The term "supramolecule" as utilized in this application refers to a molecule that is capable of interfering with the interaction between the hydrophobic substituents and the membranes of vesicles or cells. The supramolecule, however, does not affect the structure of the membrane or the hydrophobically modified polymeric matrix to which the hydrophobic substituents are attached. As a result, the biopolymeric matrix becomes disengaged from the vesicles or cells and is easily removed without damaging the cell or vesicle membranes. In one embodiment of the present invention, the supramolecules described herein are barrel-shaped molecules where the exterior of the barrel is hydrophilic while its interior pocket is hydrophobic. The hydrophobic nature of the interior pocket allows the supramolecules to interact with the hydrophobic substituents attached to the biopolymeric matrix. Some examples of such supramolecules include cyclodextrins. In one preferred embodiment, α-cyclodextrin (α-CD), β-cyclodextrin (β-CD), or γ-cyclodextrin (γ-CD) or are used as the supramolecules to reverse gelation of the biopolymeric matrix and vesicles or cells. In yet a further embodiment, methyl-β-CD, 2-hydroxypropyl-β-CD, 2-hydroxypropyl-γ-CD, sulfobutylether-β-CD, or similar variations of molecules that interfere with the interactions between the hydrophobic substituents of the polymer are utilized. These sugar-based cyclodextrins sequester polymer hydrophobic substituents within their hydrophobic pocket.[25,26] As a result, gels formed by the interaction of hydrophobically modified chitosans, alginates, and cellulosics matrices will be dissolved by the addition of the supramolecules.

As explained above, α-CD belongs to a cyclodextrin family of barrel-shaped supramolecules where the exterior of the barrel is hydrophilic, whereas its interior pocket is hydrophobic. In particular, the pocket diameter of 0.57 nm in α-CD is optimum for sequestering single-tailed hydrophobes such as those on hm-chitosan whereas the pocket is too narrow to fit two-tailed lipids from cell membranes. These molecules are soluble in water and thus can be applied to a hydrophobically-modified polymer/blood gel so as to reverse the gelation, either through an aqueous spray bottle, or simply by dispensing the α-CD containing fluid into the treated area of tissue via syringe applicator. As described in the examples below, other Cyclodextrins and supramolecules such as α-CD, β-CD, γ-CD, methyl-β-CD, 2-hydroxypropyl-β-CD, 2-hydroxypropyl-γ-CD, sulfobutylether-β-CD and other cyclodextrin derivatives that interfere with the interactions between the hydrophobic substituents and the membranes, but without harming the structure of the membranes or the hydrophobically modified biopolymer.

Figure 3:
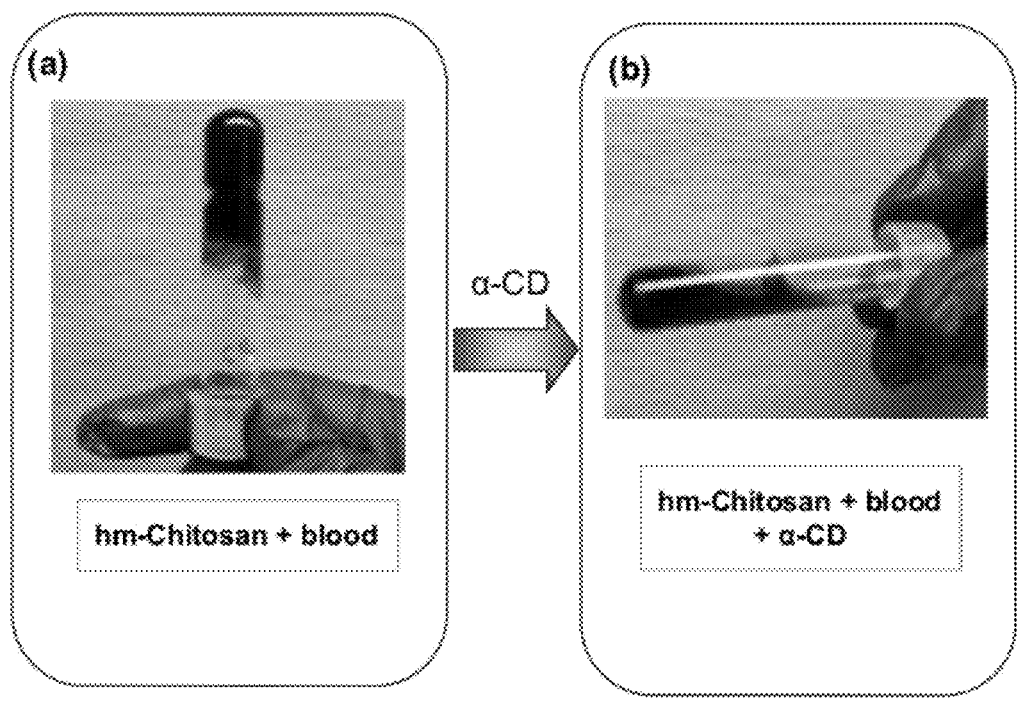
FIG. 3 is a picture that shows the effect of the addition of α-cyclodextrin to a mixture of hm-chitosan and blood.

Applicants have shown that by adding an aqueous solution of α-CD to a blood gel formed by adding hm-chitosan, the gel reverts back to a liquid-like state, as shown in FIG. 3. From visual observations, it is clear that α-CD is able to quickly reverse the gelling and convert the sample into a thin, flowing liquid or "sol." Dynamic rheology confirms these observations: the response in the presence of α-CD is liquid like with G" (viscous modulus)>G' (elastic modulus) over the range of frequencies. The hydrophobes on hm-chitosan chains are shown to be sequestered within the hydrophobic pockets of α-CD molecules. In turn, the polymer chains no longer connect adjacent cells, allowing the cells to flow freely. Effectively, the strong α-CD-to-hydrophobe affinity causes the hydrophobes to "unhook" from the cells and bind to α-CDs instead.

Applicants have also demonstrated similar effects of cyclodextrins when introduced to hm-chitosan and vesicle mixtures. Both α-CD (6 membered sugar ring molecule) and γ-CD (8 membered sugar ring molecule) are shown to reverse the gelation of vesicles by hm-chitosan as described in the examples below.

In one embodiment of the present invention, a spray formulation and applicator which contains either aqueous or powdered cyclodextrins (either α-, β-, or γ-CD) used in liquefying systems which have gelled, i.e. have become elastic solids, as a result of mixing a solution of amphiphilic polymer, e.g. hydrophobically modified chitosan, with any suspension of biological cells, e.g. blood. In other embodiments, manufactured vesicles are released from hm-chitosan, e.g., mixed surfactant vesicles or L-α-phosphatidylcholine liposomes.

The reversal of blood gelation acts as a mitigation to unwanted clotting caused by amphiphilic polymers used as hemostats. It also serves another practical application, as surgeons who receive patients treated with amphiphilic polymer for bleeding control may want to reverse the clotting action so as to remove the material in order to identify and treat the point of injury quickly and accurately. A method for treating wounds in accordance with one embodiment of the present invention consists of a first step of applying a hm-biopolymer matrix to a wound. The hm-biopolymer matrix may be in the form of a liquid, a liquid spray, sprayable foam, a gel, a dry film (alone or as part of a bandage), or lyophilized film (alone or as part of a bandage). In a second step, when medical personnel determine that the hm-chitosan should be removed, a supramolecule solution is applied to the site where the hm-chitosan was added to the wound. The supramolecule solution used is based on the type of solvent in which a supramolecule may dissolve. For example, α-CD and γ-CD are soluble in water, so a water solution is used when either of these two supramolecules is used. On the other hand, β-CD is more soluble in ethyl alcohol. Thus, a β-CD/ethyl alcohol solution is used in such an instance. It is contemplated that any combination of solute and solvent that is medically advantageous may be utilized. Other solvents include methanol and 2-propanol When blood clots (i.e., the fibrin "plug" is formed) in live specimens or patients, the method may not result in dissolution of the blood clot. However, the supramolecule solution is still used to allow removal of the hm-biopolymer from the site of the wound. By way of non-limiting example, when a bandage containing an hm-biopolymer is used to treat a wound, the bandage is soaked in the supramolecule to help release the bandage from the wound. The quantity of the supramolecule used to aid in removing such bandages varies depending on the amount of time that the bandage has been on the wound and the severity of the wound.

In one exemplary method, cyclodextrin molecules are introduced into the gel systems in aqueous solution. The molecules are delivered through a syringe or a spray apparatus. In an alternative embodiment, the supramolecules are provided in powdered form to be dissolved in an appropriate solvent before application to a gelled biopolymer matrix mixed with blood or vesicles. In yet further embodiments, the supramolecules are delivered in the form of ointments that are rubbed on the gelled clot. In some therapeutic embodiments, the supramolecules are combined with antimicrobial and antibacterial agents to further prevent infection. In one example, the supramolecules are delivered with antibacterials such as silver, norfloxacin, ampicillin or penicillin. In further embodiments, the supramolecules are delivered with biodegradable polymers like gelatin, collagen, PEG, and PLGA providing skin protection.

In one embodiment of the present invention, brief shearing of the gel allows un-gelling of the structures to occur more quickly as numerous hydrophobes become displaced from the vicinity of cell and/or vesicle bilayers and, as such, become available for interaction with cyclodextrin molecules.

Gelation is driven by the hydrophobic affinity between the grafted tails (hydrophobic substituents) on the polymer and the acyl tails of lipids in cell bilayers.[21,29] Thus, a mechanism to reverse the gelation via a species that preferentially binds to the polymer hydrophobes and thereby disengage the hydrophobic substituents from the cells is described. Applicants have demonstrated such reversal using the sugar-based supramolecule α-CD as shown below.

In one embodiment of the present invention, an in situ gelling system is provided consisting of hm-biopolymer, a supramolecule, and functionalized vesicles. In one non-limiting example, the vesicles are loaded (functionalized) with a drug, and the use of the drug is optimized by localized controlled release from within a damaged body cavity. Because the cavity is irregularly shaped, it is ideal to apply the system in liquid format, such that the liquid system could fully fill the space of the cavity. As shown in FIG. 5, the liquid forms a gel over long time scales and drug contained with the liposomes would be slowly released from the gel. Note, again in reference to FIG. 5, that dynamics of interaction between hydrophobic substituents and either cyclodextrins or membranes depend significantly upon time scale. At short time scales, mixtures of hm-chitosan+vesicles+cyclodextrin display the physical characteristics of a freely flowing liquid, whereas at long time scales these systems behave as elastic gels. Hence, at short time scales, the hydrophobes prefer interaction with the cyclodextrins, but at long time scales (on the order of days), many hydrophobes become re-entrenched into the membranes, causing the onset of gelation. This phenomenon presents the potential usefulness of the hm-chitosan+vesicle+cyclodextrin mixture as an in situ gelling system.

Similar in situ gelling scenarios may be useful for tissue engineering applications. It may be desired to recruit specific cell types into the damaged body cavity. As such, the vesicles may be loaded with growth factor, for slow and sustained release after gelation of the hm-chitosan+vesicle+supramolecule system. Alternately, cells are included in the initial cocktail so as to achieve the desired therapeutic effect. In this case, the cells are mixed with the hm-chitosan+vesicles+supramolecule and delivered into the irregularly shaped injury. After gelation of the system, the cells may operate to repair the surrounding damaged tissue.

One embodiment of the present invention provides for a method for reversing the interaction between a hydrophobically modified polymeric matrix (e.g., hm-chitosan) and membranes (cell membranes or vesicle membranes), which form a gelled matrix. In accordance with the method a supramolecule capable of disrupting interactions between hydrophobic substituents on the hydrophobically modified polymeric matrix is applied to the gelled matrix. As described above, in one embodiment, the supramolecule is a cyclodextrin, which may be selected from the group consisting of α-CD, β-CD, γ-CD, methyl-β-CD, 2-hydroxypropyl-β-CD, 2-hydroxypropyl-γ-CD, sulfobutylether-β-CD and other cyclodextrin derivatives. In a further embodiment, a method for treating wound bleeding is provided in which a hydrophobically modified polymer is applied to a wound. When the hydrophobically modified polymer needs to be removed, the supramolecule solution is applied to the site of the wound.

A further embodiment of the present invention provides a kit for treating wounds or releasing vesicles from a hydrophobically modified polymeric matrix. The kit has several components, including a hydrophobically modified polymeric matrix for application to a wound and a supramolecule solution to reverse the interactions between the cells at the wound site and the hydrophobically modified polymeric matrix. The hydrophobic polymeric matrix may be provided in the form of a gel, spray, or bandage, as described in United States Patent Application Publication Numbers US2008/0254104A1 and US2009/0062849A1. The supramolecule, such as any of the cyclodextrins or cyclodextrin derivatives described above, are provided in various different forms. For example, the supramolecule is provided in powder form for mixing with a solvent before application to the wound or hydrophobically modified polymeric matrix loaded with vesicles. The supramolecule in another example, is provided in the form of a liquid solution.

In yet another preferred embodiment, a vesicle+hm-polymer gel may be applied over the exposed area of a chronic wound (e.g. diabetic ulcer). The vesicles may be pre-loaded with growth factor for slow and sustained release, so as to accelerate healing of the wound. Once the wound is healed, the gel is dissolved and washed away by application of a supramolecule, e.g., cyclodextrin, solution via spray bottle, a syringe or any other method that allows the solution to be delivered to the gelled compound.

EXAMPLES

Materials.

Chitosan of medium molecular weight (190-310K) and Brookfield viscosity of 286 cps was purchased from Sigma-Aldrich. The reported degree of deacetylation was about 80-%. Chitosan was dissolved in 0.15 M of either L-lactic acid or acetic acid (both from Sigma-Aldrich) so as to mimic physiological ionic strength. The supramolecules α-CD and γ-CD were purchased from TCI.

Synthesis of hm-Chitosan.

hm-chitosan was synthesized by attaching benzene-n-octadecyl tails to the chitosan backbone via reaction with 4-octadecylbenzaldehyde (purchased from TCI). The procedure is identical to that used in our earlier paper[21] and it also follows those described in the literature[20]. The degree of hydrophobic substitution follows the reaction stoichiometry and, here, hm-chitosans of 1.5 and 2.5 mol % of the available amine groups were prepared.

Obtaining Blood.

5 human subjects volunteered to have 20 mL of blood drawn by a registered nurse at the UMD School of Medicine.

Subjects were healthy adults ranging age from 20 to 40 years of age (4 males, 1 female). 10 mL intervals of blood were drawn into Becton Dickinson Vacutainers® containing 143 USP units of sodium heparin. The protocol was approved by the Institutional Research Board (IRB) at UMD.

Preparation of Vesicles.

The surfactant system employed was a mixture of the cationic surfactant, cetyl trimethylammonium tosylate (CTAT), and the anionic surfactant, sodium dodecyl benzene sulfonate (SDBS). The surfactants were purchased from Aldrich, and all solutions were made using distilled-deionized water. The phase diagram for CTAT/SDBS mixtures has been reported previously.[31] To form vesicles, CTAT and SDBS were mixed at a weight ratio of 70/30, respectively, at a combined 2 wt % concentration in water. The mixture was stirred overnight to ensure complete dissolution and equilibration of the vesicles prior to experiments.

Rheological Experiments:

Steady and dynamic rheological experiments were performed on a Rheometrics AR2000 stress-controlled rheometer. A cone-and-plate geometry of 40 mm diameter and 4° cone angle was used and samples were run at the physiological temperature of 37° C. Dynamic frequency spectra were obtained in the linear viscoelastic regime of the samples, as determined from dynamic strain sweep experiments.

Results

Figure 2A:
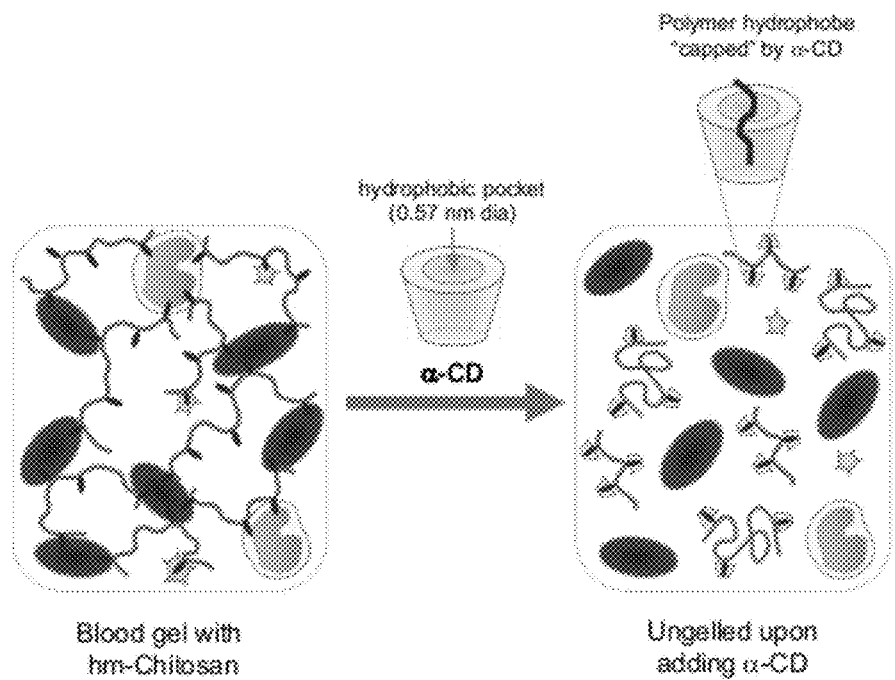
FIG. 2A is a graphical representation of a method for reversing blood gelation in accordance with one embodiment of the present invention.
Figure 2B:
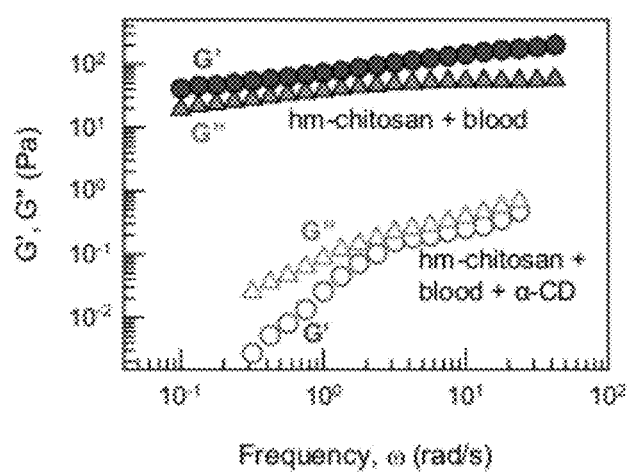
FIG. 2B is a dynamic rheology chart that demonstrates reversal of gelation of blood and hm-chitosan by the addition of a supramolecule such as cyclodextrin.

FIG. 2 shows the result of adding 3 wt % of α-CD to a blood gel formed by adding 0.25 wt % hm-chitosan. From visual observations, it was clear that the α-CD was able to instantly reverse the gelling and convert the sample into a thin, flowing liquid or "sol". Dynamic rheology confirms these observations: note from FIG. 2 that the response in the presence of α-CD is liquid-like with G">G' over the frequency range. FIG. 2 also presents a schematic illustrating the action of α-CD: here, the hydrophobes on hm-chitosan chains are shown to be sequestered within the hydrophobic pockets of α-CD molecules. In turn, the polymer chains no longer connect adjacent cells, allowing the cells to flow freely. Effectively, the strong affinity of α-CD for the hydrophobes causes these moieties to "unhook" from the cells and bind to the α-CDs instead. Note that the results with α-CD further demonstrate that free hydrophobes are required for gelation, as depicted in FIG. 1.

FIG. 3 is a visual representation of the rheological results presented in FIG. 2. FIG. 3(a) is a photograph of human heparinized blood gelled by 0.25 wt % hm-chitosan. The mixture is elastic and holds its own weight upon vial inversion. In contrast, the introduction of 3 wt % α-CD to the mixture in FIG. 3(b) results in the disruption of the gel into a freely flowing viscous liquid. Note that this sample cannot hold its own weight upon vial inversion.

In FIGS. 4-7, hm-chitosan is mixed with vesicles instead of blood. It is important to note that vesicles have a great deal of structural similarity with cells: both are water-enclosed bilayers. A key difference is that vesicles are significantly smaller than cells with sizes on the order of 100 nm. In contrast, red blood cells are ~8 μm in size. These experiments show that the supramolecules work both in cells and vesicles.

Figure 4:
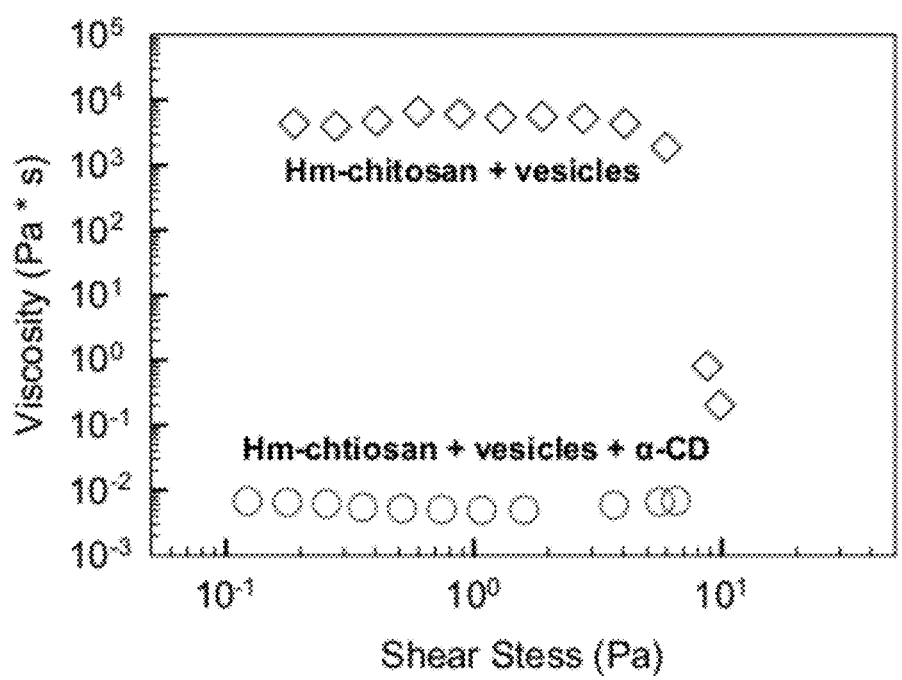
FIG. 4 is a steady-state rheology chart of hm-chitosan with vesicles in the presence or absence of α-cyclodextrin.

FIG. 4 displays the steady shear rheology of two samples which were prepared by mixing aqueous solutions of hm-chitosan (benz-C18, 1.5% modified), vesicles (70/30 CTAT/SDBS) and α-CD. The concentrations of hm-chitosan and vesicles were held constant at 0.238 wt % and 0.952 wt %, respectively, in both samples. One sample contained 0 mM α-CD (open diamonds) and the other contained 28.6 mM α-CD (open circles). The sample containing no α-CD showed a zero-shear viscosity approaching $10^4$. In contrast, the α-CD-containing sample showed a zero-shear viscosity approaching $10^{-2}$, a viscosity drop on the order of a million-fold.

Figure 5:
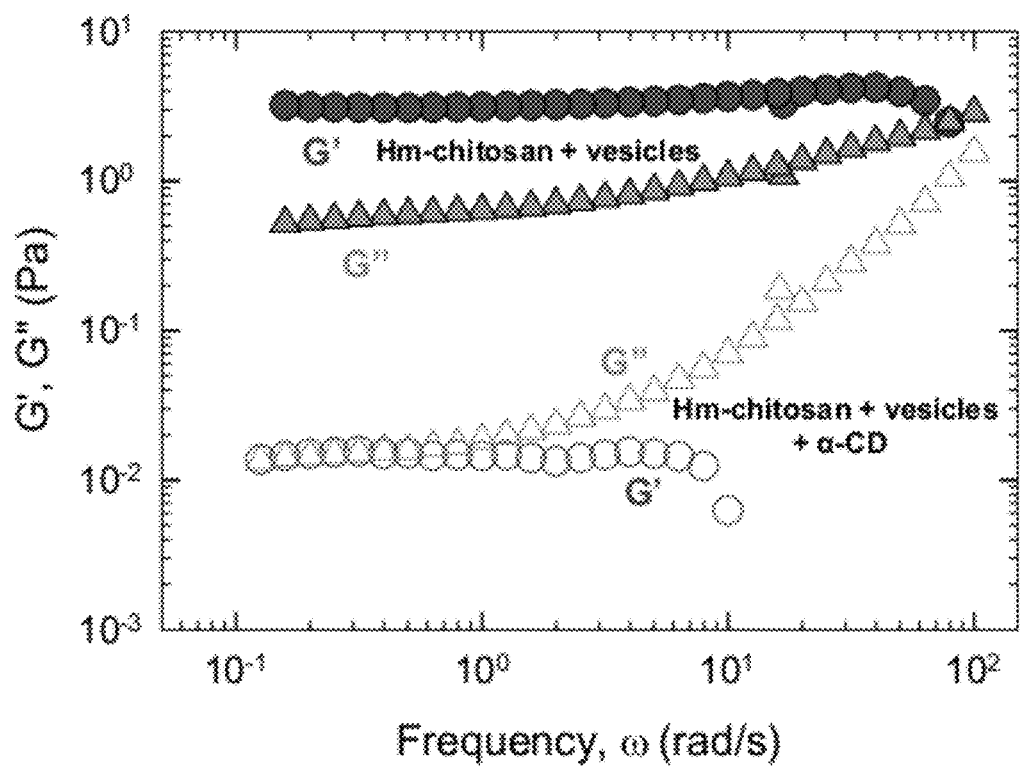
FIG. 5 is a dynamic rheology chart of hm-chitosan with vesicles in the presence or absence of α-cyclodextrin.

FIG. 5 shows the dynamic rheology of the same two samples. The initial gel based on hm-chitosan and vesicles shows an elastic, gel-like response (closed symbols), with G'>G" over the range of frequencies and both G' and G" becoming independent of frequency as $\omega \rightarrow 0$. In contrast, upon addition of 28.6 mM α-CD to the mixture, the response converts to that of a viscous liquid (open symbols), with G"<G' over the range of frequencies. As $\omega \rightarrow 0$, G' and G" are observed to overlap, indicating the onset of gelation over long time scales. However, at practical time scales, the hm-chitosan+vesicle+α-CD mixture behaves as a freely flowing liquid.

Figure 6:
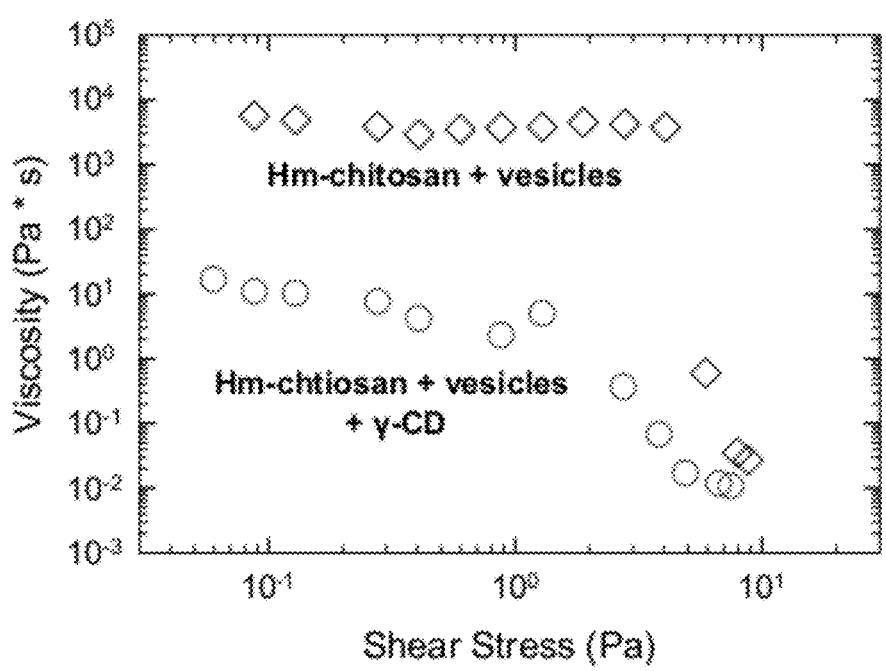
FIG. 6 is a steady-state rheology chart of hm-chitosan with vesicles in the presence or absence of γ-cyclodextrin.
Figure 7:
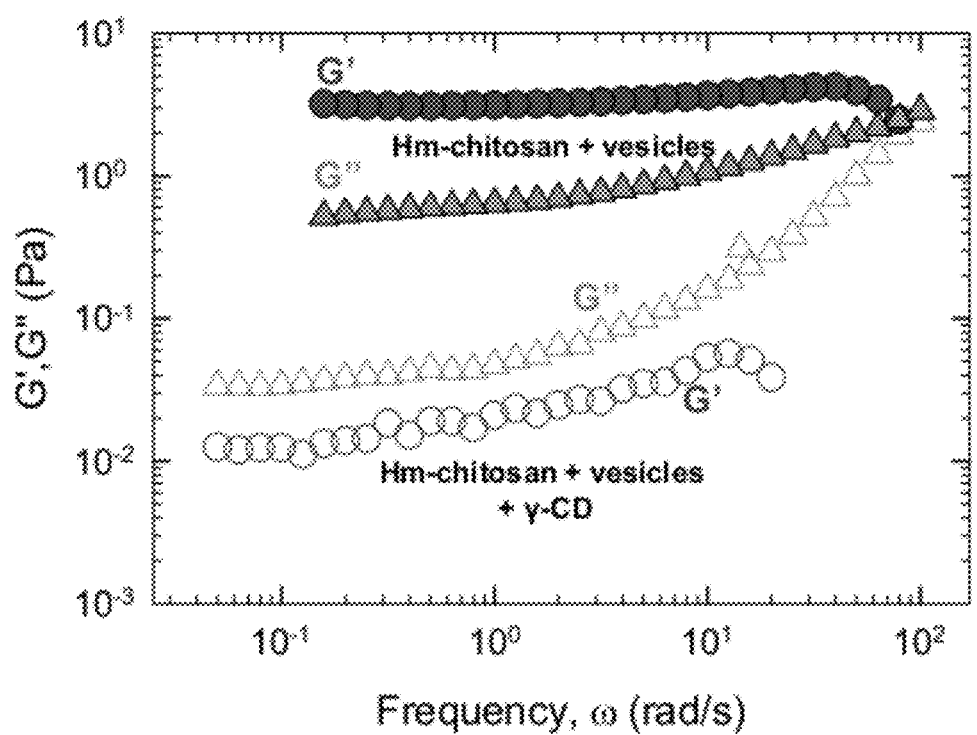
FIG. 7 is a dynamic rheology chart of hm-chitosan with vesicles in the presence or absence of γ-cyclodextrin.

FIGS. 6 and 7 explore the use of γ-cyclodextrin, instead of α-CD, in conjunction with hm-chitosan and vesicles. Again, two samples were prepared by mixing aqueous solutions of hm-chitosan (benz-C18, 1.5% modified), vesicles (70/30 CTAT/SDBS) and γ-CD. The concentrations of hm-chitosan and vesicles were held constant at 0.238 wt % and 0.952 wt %, respectively, in both samples. One sample contained 0 mM γ-CD (open diamonds) and the other contained 28.6 mM γ-CD (open circles). In FIG. 6, we find that the sample containing no γ-CD showed a zero-shear viscosity approaching $10^4$. In contrast, the γ-CD-containing sample showed a zero-shear viscosity approaching $10^1$, a viscosity drop on the order of a thousand-fold. While the addition of γ-CD causes a significant drop in the apparent viscosity of the sample, this drop is still a thousand-fold lower in magnitude relative to the drop caused by the addition α-CD. This difference may be attributed to a better geometric fit between the α-CD and the single tailed benzyl-$C_{18}$ hydrophobe, as compared to that of γ-CD and the same single-tailed hydrophobe.

In FIG. 7, the same two samples described in FIG. 6 are characterized by dynamic rheology. The initial gel based on hm-chitosan and vesicles shows an elastic, gel-like response (closed symbols), whereas upon addition of 28.6 mM γ-CD, the response converts to that of a viscous liquid (open symbols). with G'>G" over the range of frequencies and both G' and G" becoming independent of frequency as $\omega \rightarrow 0$. In contrast, upon addition of 28.6 mM γCD to the mixture, the response converts to that of a viscous liquid (open symbols), with G"<G' over the range of frequencies. As $\omega \rightarrow 0$, G' and G" are not observed to overlap, indicating that the sample does not become more gel-like as $t \rightarrow \infty$.

The invention has been described with references to a preferred embodiment. While specific values, relationships, materials and steps have been set forth for purposes of describing concepts of the invention, it will be appreciated by persons skilled in the art that numerous variations and/or modifications may be made to the invention as shown in the specific embodiments without departing from the spirit or scope of the basic concepts and operating principles of the invention as broadly described. It should be recognized that, in the light of the above teachings, those skilled in the art can modify those specifics without departing from the invention taught herein. Having now fully set forth the preferred embodiments and certain modifications of the concept underlying the present invention, various other embodiments as well as certain variations and modifications of the embodiments herein shown and described will obviously occur to those skilled in the art upon becoming familiar with such underlying concept. It is intended to include all such modifications, alternatives and other embodiments insofar as they come within the scope of the appended claims or equivalents thereof. It should be understood, therefore, that the invention may be practiced otherwise than as specifically set forth herein. Consequently, the present embodiments are to be considered in all respects as illustrative and not restrictive.

REFERENCES

All references cited below and within the description above are incorporated herein by reference in their entirety.
[1] Owen, C. A. *A History of Blood Coagulation*; Mayo Foundation: Rochester, Minn., 2001.
[2] Macfarlane, R. G. "An enzyme cascade in the blood clotting mechanism, and its function as a biological amplifier." *Nature* 1964, 202, 498-499.
[3] Smith, G. F. "Fibrinogen-fibrin conversion—Mechanism of fibrin-polymer formation in solution." *Biochem. J.* 1980, 185, 1-11.
[4] Doolittle, R. F. "Fibrinogen and fibrin." *Annu. Rev. Biochem.* 1984, 53, 195-229.
[5] Neuffer, M. C.; McDivitt, J.; Rose, D.; King, K.; Cloonan, C. C.; Vayer, J. S. "Hemostatic dressings for the first responder: A review." *Military Med.* 2004, 169, 716-720.
[6] Larson, M. J.; Bowersox, J. C.; Lim, R. C.; Hess, J. R. "Efficacy of a fibrin hemostatic bandage in controlling hemorrhage from experimental arterial injuries." *Arch. Surg.* 1995, 130, 420-422.
[7] Reiss, R. F.; Oz, M. C. "Autologous fibrin glue: Production and clinical use." *Transfusion Med. Rev.* 1996, 10, 85-92.
[8] Champion, H. R.; Bellamy, R. F.; Roberts, C. P.; Leppaniemi, A. "A profile of combat injury." *J. Trauma* 2003, 54, S13-S19.
[9] Stewart, R. M.; Myers, J. G.; Dent, D. L.; Ermis, P.; Gray, G. A.; Villarreal, R.; Blow, O.; Woods, B.; McFarland, M.; Garavaglia, J.; Root, H. D.; Pruitt, B. A. "Seven hundred fifty-three consecutive deaths in a level 1 trauma center: The argument for injury prevention." *J. Trauma* 2003, 54, 66-70.
[10] Kauvar, D. S.; Lefering, R.; Wade, C. E. "Impact of hemorrhage on trauma outcome: An overview of epidemiology, clinical presentations, and therapeutic considerations." *J. Trauma* 2006, 60, S3-S9.
[11] Kheirabadi, B. S.; Acheson, E. M.; Deguzman, R.; Sondeen, J. L.; Ryan, K. L.; Delgado, A.; Dick, E. J.; Holcomb, J. B. "Hemostatic efficacy of two advanced dressings in an aortic hemorrhage model in swine." *J. Trauma* 2005, 59, 25-34.
[12] Pusateri, A. E.; Holcomb, J. B.; Kheirabadi, B. S.; Alam, H. B.; Wade, C. E.; Ryan, K. L. "Making sense of the preclinical literature on advanced hemostatic products." *J. Trauma* 2006, 60, 674-682.
[13] Arnaud, F.; Teranishi, K.; Tomori, T.; Carr, W.; McCarron, R. "Comparison of 10 hemostatic dressings in a groin puncture model in swine." *J. Vascular Surg.* 2009, 50, 632-639.
[14] Kheirabadi, B. S.; Scherer, M. R.; Estep, J. S.; Dubick, M. A.; Holcomb, J. B. "Determination of Efficacy of New Hemostatic Dressings in a Model of Extremity Arterial Hemorrhage in Swine." *J. Trauma* 2009, 67, 450-460.
[15] Bochicchio, G.; Kilbourne, M.; Kuehn, R.; Keledjian, K.; Hess, J.; Scalea, T. "Use of a modified chitosan dressing in a hypothermic coagulopathic grade V liver injury model." *Am. J. Surg.* 2009, 198, 617-622.
[16] Ellis-Behnke, R. G.; Liang, Y.-X.; Tay, D. K. C.; Kau, P. W. F.; Schneider, G. E.; Zhang, S.; Wu, W.; So, K.-F. "Nano hemostat solution: Immediate hemostasis at the nanoscale." *Nanomedicine* 2006, 2, 207-215.
[17] Ellis-Behnke, R. G.; Liang, Y. X.; You, S. W.; Tay, D. K. C.; Zhang, S. G.; So, K. F.; Schneider, G. E. "Nano neuro knitting: Peptide nanofiber scaffold for brain repair and axon regeneration with functional return of vision." *Proc. Natl. Acad. Sci. U.S.A.* 2006, 103, 5054-5059.
[18] Lew, W. K.; Weaver, F. A. "Clinical use of topical thrombin as a surgical hemostat." *Biologics* 2008, 2, 593-599.
[19] Kean, T.; Thanou, M. "Biodegradation, biodistribution and toxicity of chitosan." *Adv. Drug Deliv. Rev.* 2010, 62, 3-11.
[20] Desbrieres, J.; Martinez, C.; Rinaudo, M. "Hydrophobic derivatives of chitosan: Characterization and rheological behaviour." *Int. J. Biol. Macromol.* 1996, 19, 21-28.
[21] Lee, J. H.; Gustin, J. P.; Chen, T. H.; Payne, G. F.; Raghavan, S. R. "Vesicle-biopolymer gels: Networks of surfactant vesicles connected by associating biopolymers." *Langmuir* 2005, 21, 26-33.
[22] Malette, W. G.; Quigley, H. J.; Gaines, R. D.; Johnson, N. D.; Rainer, W. G. "Chitosan: A new hemostatic." *Ann. Thorac. Surg.* 1983, 36, 55-58.
[23] Rao, S. B.; Sharma, C. P. "Use of chitosan as a biomaterial: Studies on its safety and hemostatic potential." *J. Biomed. Mater. Res.* 1997, 34, 21-28.
[24] Whang, H. S.; Kirsch, W.; Zhu, Y. H.; Yang, C. Z.; Hudson, S. M. "Hemostatic agents derived from chitin and chitosan." *J. Macromol. Sci.-Polym. Rev.* 2005, C45, 309-323.
[25] Szejtli, J. "Introduction and general overview of cyclodextrin chemistry." *Chem. Rev.* 1998, 98, 1743-1753.
[26] Tonelli, A. E. "Nanostructuring and functionalizing polymers with cyclodextrins." *Polymer* 2008, 49, 1725-1736.
[27] Raghavan, S. R.; Cipriano, B. H. Gel formation: Phase diagrams using tabletop rheology and calorimetry. In *Molecular Gels*; Weiss, R. G., Terech, P., Eds.; Springer: Dordrecht, 2005; pp 233-244.
[28] Macosko, C. W. *Rheology: Principles, Measurements and Applications*; VCH Publishers: New York, 1994.
[29] Meier, W.; Hotz, J.; GuntherAusborn, S. "Vesicle and cell networks: Interconnecting cells by synthetic polymers." *Langmuir* 1996, 12, 5028-5032.
[30] Kumar, R.; Raghavan, S. R. "Thermothickening in solutions of telechelic associating polymers and cyclodextrins." *Langmuir* 2010, 26, 56-62.
[31] Kohler et al, *J. Phys. Chem. B,* 2000, 104, 11305

What is claimed is:
1. A method for reversing gelling of a hydrophobically modified biopolymer and a cellular membrane, comprising:
   applying a supramolecule to a gel formed by interaction between the hydrophobically modified biopolymer and the membrane, whereby the gel is converted into a flowing liquid and the gelling of the biopolymer and the membrane is reversed.
2. The method of claim 1, wherein the supramolecule is a cyclodextrin.
3. The method of claim 2, wherein the cyclodextrin is selected from the group consisting of α-cyclodextrin, β-cyclodextrin, γ-cyclodextrin, methyl-β-cyclodextrin, 2-hydroxypropyl-β-cyclodextrin, 2-hydroxypropyl-γ-cyclodextrin, sulfobutylether-β-cyclodextrin and other cyclodextrin derivatives.
4. The method of claim 1, wherein said supramolecule is applied to the gel by a syringe or a spray bottle.
5. The method of claim 1, wherein the supramolecule is dissolved in a solvent.

6. The method of claim 5, wherein the solvent is selected from the group consisting of water, ethyl-alcohol, methanol, and 2-propanol.

7. The method of claim 5, wherein the hydrophobically modified biopolymer is selected from the group consisting of chitosans, alginates, and cellulosics.

8. A kit for treating wounds, comprising: a hydrophobically modified biopolymer, and a supramolecule capable of reversing gelling of a gel formed by interaction between the hydrophobically modified biopolymer and a cellular membrane, whereby the gel is converted into a flowing liquid and the gelling of the biopolymer and the membrane is reversed.

9. The kit of claim 8, wherein the hydrophobically modified biopolymer is selected from the group consisting of chitosans, alginates, and cellulosics.

10. The kit of claim 8, wherein the supramolecule is a cyclodextrin.

11. The kit of claim 8, wherein the cyclodextrin is selected from the group consisting of α-cyclodextrin, β-cyclodextrin, γ-cyclodextrin, methyl-β-cyclodextrin, 2-hydroxypropyl-β-cyclodextrin, 2-hydroxypropyl-γ-cyclodextrin, sulfobutylether-β-cyclodextrin and other cyclodextrin derivatives.

12. The kit of claim 8, wherein said supramolecule is applied to the gel by a syringe or a spray can.

13. The kit of claim 8, wherein the supramolecule is dissolved in a solvent selected from the group consisting of water, ethyl-alcohol, methanol, and 2 propanol.

14. The kit of claim 8, wherein the supramolecule is provided as a liquid or dry powder.

15. The kit of claim 14, further comprising a solvent.

16. The kit of claim 8, wherein the hydrophobically modified biopolymer has hydrophobic substituents connected to functionalized vesicles.

17. The kit of claim 8, wherein the functionalized vesicles contain medications for release at the site where the hydrophobically modified biopolymer is placed.

* * * * *